United States Patent [19]

Bourdon

[11] 4,323,066
[45] Apr. 6, 1982

[54] SYRINGE

[76] Inventor: Frédéric Bourdon, 51, Aristide Briand St., 92300 Levallois, France

[21] Appl. No.: 190,259

[22] Filed: Sep. 24, 1980

[30] Foreign Application Priority Data

Nov. 6, 1979 [FR] France ................................ 79 27275

[51] Int. Cl.³ ............................................. A61M 5/00
[52] U.S. Cl. ................................ 128/218 R; 128/234; 128/276
[58] Field of Search ......... 128/218 R, 218 P, 218 PA, 128/218 A, 223, 224, 276, 234, 215; 222/386, 387

[56] References Cited

U.S. PATENT DOCUMENTS 3,279,659 10/1966 Harris, Jr. ..................... 128/234 X
3,306,502  2/1967 Harris, Jr. ..................... 222/386
3,605,746  9/1971 Hodosh ......................... 128/218 A
3,818,907  6/1974 Walton .......................... 128/234 X

FOREIGN PATENT DOCUMENTS 2193626 2/1974 France .
16647 of 1911 United Kingdom .

Primary Examiner—John D. Yasko
Attorney, Agent, or Firm—Sandler & Greenblum

[57] ABSTRACT

Apparatus for injecting or aspirating a fluid, including a liquid or paste. The apparatus includes a first piston adapted to be in direct contact with the fluid; and a second piston comprising a shaft adapted to coact with the first piston. The second piston is slideably mounted in a cylinder. The cylinder is divided by the second piston into a first chamber situated on the fluid injection side of the cylinder and a second chamber situated on the opposite side of the cylinder. The cylinder is adapted to be in fluid communication with a positive or negative pressure. At least one communication channel is positioned between the second chamber and the exterior of the cylinder. The at least one channel has a chamber orifice opening into the second chamber and an exterior orifice opening to the exterior. Blocking means for blocking the channel are also provided. The apparatus is such that a positive or negative pressure in the second chamber relative to the first chamber while the communication channel is blocked results in the controllable movement of the first piston.

19 Claims, 4 Drawing Figures

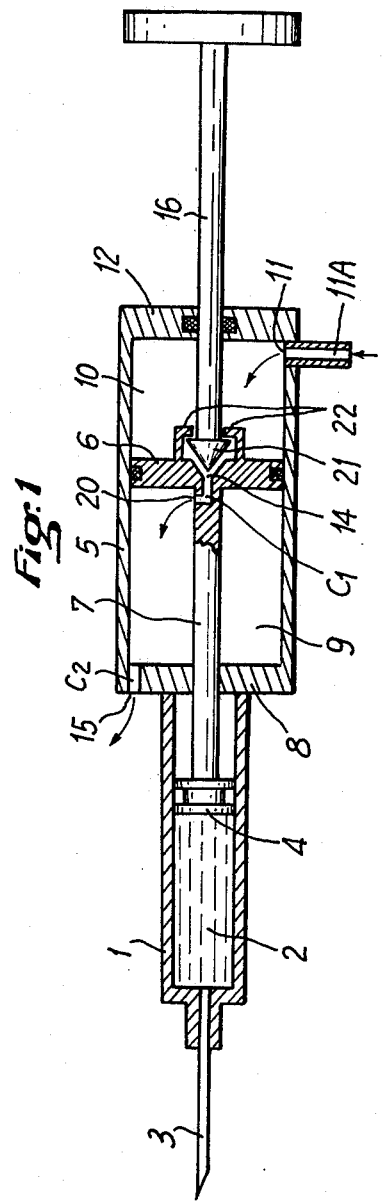
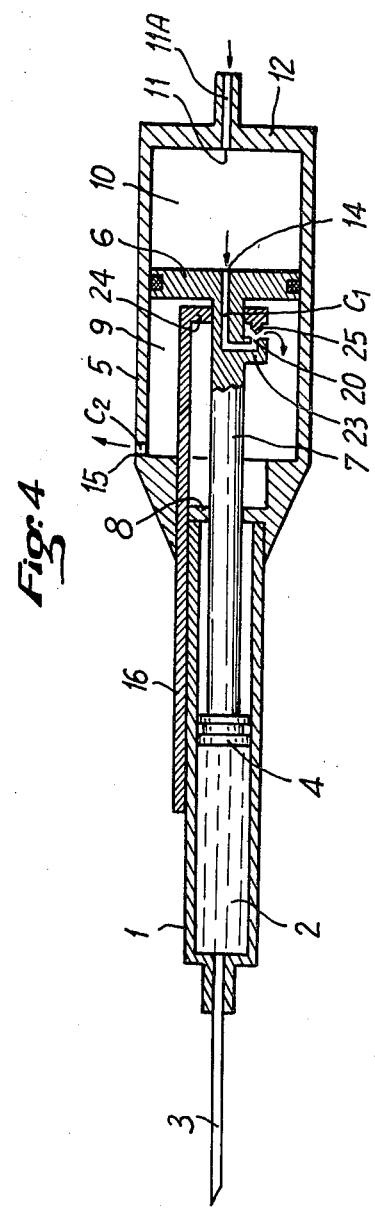

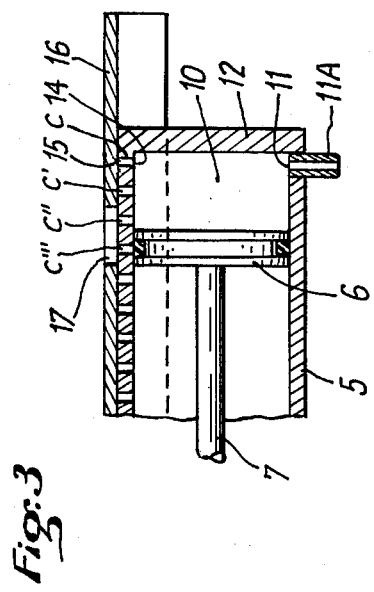
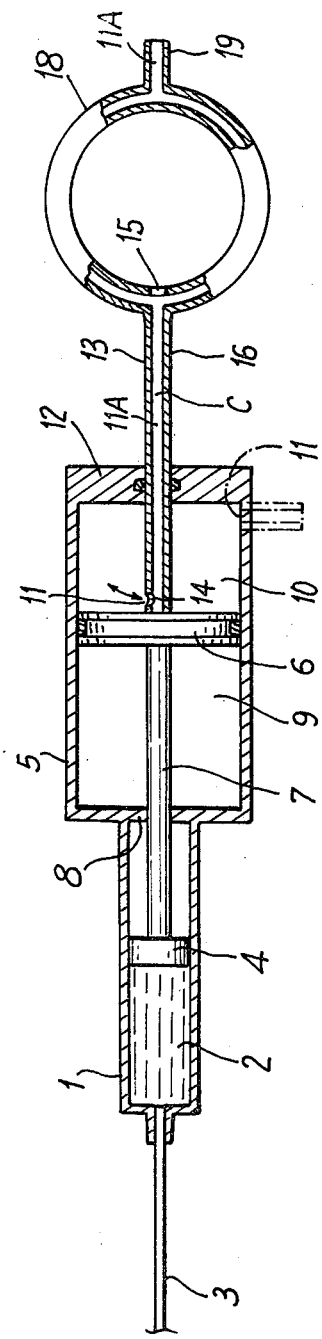

SYRINGE

BACKGROUND OF THE INVENTION

1. Field of the Invention

The invention relates to an apparatus for ejecting a fluid material. In particular the invention relates to a syringe in which a pressurized hydraulic fluid is adapted to furnish the force necessary to eject a liquid a material.

Such a syringe is very useful when injecting a fluid, such as a liquid, into compact tissue where liquid diffusion is poor, such as for example, in bone tissue, as is often a problem in dental surgery. However, the syringe of the invention is not limited to this use and, on the contrary, extends by virtue of its novel design to a very wide variety of possible uses. In effect, the syringe also makes it possible to inject into soft tissue with the same softness and the same degree of precise control which one is able to achieve with purely manual syringes. Also, the syringe can be used for the injection of a liquid into tissue without a needle, by simple projection of the liquid under high pressure.

2. Description of Prior Art

Hydraulic syringes are known and are shown, for example, in U.S. Pat. No. 3,605,745 and in French Pat. No. 72 27030 (2,193,626). In these syringes The system comprises a hydraulic pressure system which itself comprises a piston on which a pressurized fluid acts. So as to provide most effective control over the pressure, the fluid is admitted on both sides of the piston and it is the differential pressure which is created between the two sides which causes the displacement of the piston in the direction of injection. The differential pressure occurs as a result of adjustment by the user of a blocking valve or of the opening of a drain orifice. This valve has a short extent. Furthermore, its open position is totally independent of the position of the jack piston, and, as a result, it is independent of the quantity of liquid to be injected. The user is, therefore, unaware of the actual speed of injection as well as the volume being injected at a given moment.

SUMMARY OF THE INVENTION

It is an object of the invention to provide an apparatus from which a fluid such as paste, or liquid, by be dispensed by means of a pressurized fluid acting on a piston. It is an object of the invention that the fluid be dispensed while under the manual control of the user such that the rate and extent of injection may be easily controlled.

It is thus a principal aim of the invention to provide a syringe which is assisted by a hydraulic or other jack in which the user is informed at any given moment of the volume being injected as well as of the velocity of injection. Furthermore, with the syringe of the invention, the user is able to himself regulate, from start to finish, the speed at which injection occurs. In fact, using the device of the invention, the user is able to set and modify, as desired, at any time, the velocity or, what amounts to the same thing in this instance, the flow rate of the liquid or other fluid.

Thus, according to the invention an apparatus for injecting or aspirating a fluid including a paste is provided which comprises a first piston adapted to be in direct contact with the fluid; and a second piston comprising a shaft adapted to coact with the first piston. The second piston is slideably mounted in a cylinder; the cylinder being divided by the second piston into a first chamber situated on the fluid injection side of the cylinder and a second chamber situated on the opposite side. The cylinder is adapted to be in fluid communication with a positive or negative pressure. At least one communication channel is positioned between the second chamber and the exterior of the cylinder. The at least one communication channel has a chamber orifice opening into the second chamber and an exterior orifice opening to the exterior. Means are provided for blocking the at least one channel. As a result of the inventive structure, a positive or negative pressure in the second chamber relative to the first chamber while the channel is blocked results in the controlable movement of the first piston.

According to a preferred embodiment of the invention the apparatus is adapted for use as a syringe and the shaft is adapted to push the first piston to inject the fluid in response to a positive pressure within the second chamber.

A variety of blocking means may be used for blocking or disengaging at least one of the chamber or exterior orifices. The blocking means may be in the form of a mobile element; the mobile element being adapted to move relative to the cylinder to block or disengage the orifices of the channel.

According to one embodiment of the invention, the mobile element extends beyond the second piston and outside of the cylinder. In this embodiment the channel extends into the shaft of the second piston and the exterior orifice is positioned on the outside of the cylinder. In effect, the communication channel comprises a first section extending between the second chamber and the first chamber, with the communication channel passing through the second piston, and a second section passing through the wall of the cylinder between the first chamber and the exterior of the cylinder. In this instance, the mobile element passes through the end wall of the cylinder opposite to the injection side and ends on the interior of the cylinder in an end adapted to block the orifice of the communication channel opening into the second chamber. The first section of the channel is coaxially bored in the piston and in the shaft of the piston and opens onto the lateral surface of the piston shaft on the interior of the first chamber. In this device, the mobile element is in effect a plunger adapted to cooperate with the second piston; said plunger being adapted to extend outside of the cylinder. The plunger ends in a conical member adapted to block the chamber orifice. The conical member is held by a plurality of fingers extending from the second piston whereby the plunger and second piston move in phase with one another.

According to an alternative embodiment of the invention, the mobile element is a shaft which extends outside of the cylinder in the form of a circular element. In this embodiment, the channel extends into the shaft of the mobile element and the circular element comprises the exterior orifice whereby the channel may be blocked by placing a thumb over the exterior orifice. The shaft of the mobile element may further comprises an orifice for feeding pressurized fluid into the channel to pressurize the second chamber.

In a third embodiment of the invention, the exterior orifice is constituted by a plurality of orifices on the wall of said cylinder. In this device the mobile element is a sleeve comprising a window. The sleeve is adapted to slide over the exterior orifices whereby registration of the window with one of the exterior orifices results in the unblocking of the exterior orifice.

According to a fourth embodiment of the invention, the mobile element passes through the end wall of the cylinder from the injection side and extends outside of the cylinder and parallel thereto. The mobile element comprises a blocking element on the interior of the cylinder. The blocking element is adapted to block the opening of the first section on the interior of the first chamber. As in the first embodiment, the first section of the communication channel is bored coaxially in the shaft of the second piston. The shaft has a radial extension facing the piston. The first section continues into the radial extension and ends in an opening in a surface facing the second piston. The mobile element extends to face this opening with a projecting portion adapted to move against said piston opening to block the opening. The mobile element is provided at its end positioned within the cylinder with a small collar slideably mounted on the piston shaft between the piston and the radial extension. The projecting portion is mounted on the radial collar.

BRIEF DESCRIPTION OF THE DRAWINGS

The invention will now be described with respect to various non-limiting embodiments in the annexed drawings, in which:

FIG. 1 is a cross sectional view along a plane passing through the longitudinal axis of a syringe according to the invention;

FIG. 2 is a view analogous to FIG. 1 of a first alternative embodiment of the syringe;

FIG. 3 is partial view in cross section illustrating a second alternative embodiment; and FIG. 4 is cross sectional view similar to that of FIGS. 1 and 2 illustrating a preferred third alternative embodiment of the invention.

DESCRIPTION OF PREFERRED EMBODIMENT

According to the invention, a syringe for injection of a liquid contained in a cartridge by virtue of a first piston in direct contact with this liquid is provided. This first piston is pushed by the shaft of a second piston slideably mounted in a cylinder which forms a portion of the syringe. This second piston divides the cylinder into a first chamber situated on the side of the liquid to be injected and into a second chamber situated on the opposite side. A feed orifice for a fluid under pressure opens into the second chamber through the wall of the cylinder.

According to the invention, at least one communication channel exists between the second chamber and the exterior of the cylinder. This channel, or each of these communication channels, has an inlet orifice opening into the second chamber and an outlet orifice opening to the exterior. One of these two orifices, is situated in a fashion so as to be blocked or disengaged at will by the user during the displacement of an mobile element mounted so as to be moveable with respect to the cylinder corresponding to the movements of the second piston.

In one embodiment of the invention, the communication channel extends into the shaft of the second piston and its outlet orifice is positioned along an extension of this shaft outside of the cylinder.

Preferably, in another embodiment of the invention, the communication channel comprises a first section extending between the second chamber and the first chamber and passing through the second piston and/or the shaft of this second piston, and second section which passes through the wall of the cylinder between the first chamber and the exterior of the cylinder.

According to an alternative embodiment, the mobile element extends through the end wall of the cylinder opposite to the injection and, this shaft ends at the interior of the cylinder with an end adapted to block the inlet orifice of the communication channel opening into the second chamber.

According to another embodiment, the mobile element extends through the end wall of the cylinder at the injection side and it is provided on the interior of the cylinder with a blocking element of the opening orifice of the first section on the interior of the first chamber. Preferably, in this embodiment, the opening orifice of the first section of the communication channel is positioned on a surface, directed torwards the piston, of a radial extension of the shaft of the piston and the mobile element is provided on the interior of the cylinder with a small collar slideably mounted on the piston shaft between this poston and the radial extension.

The examples described above all fall within the general concept of the invention. Quite obviously, the general concept of the invention may be modified as needed without going beyond the scope of the invention. Identical or corresponding elements in each of the various drawings, have been identified by like numerals.

With reference to FIG. 1 an injection syringe comprises a cylinder 1 or a separate cartridge 1 containing a liquid 2 to be injected 2 through a needle 3 under pressure from a first piston 4 which is in direct contact with the liquid 2. The syringe also comprises behind the cylinder 1 or the cartridge 1, a cylinder 5 of a pressure jack comprising a second piston 6. This piston is mounted at one end of a piston shaft 7 which extends through the end wall 8 on the side of a needle 3 or, more generally, from the liquid injection side to outside of the cartridge 1. The other end of the piston shaft 7 acts directly on the first piston 4.

The second piston 6 divides the cylinder 5 of the jack into a first chamber 9 situated on the side of the liquid 2 to be injected and a second chamber 10 situated on the opposite side. A feed orifice 11 for feeding fluid under pressure (preferably compressed gas) opens into the second chamber 10. The exact position of this orifice is not critical as long as the second chamber 10 can be appropriately fed. Orifice 11 can be that of a channel 11A extending through the lateral walls of the cylinder 5 as shown in solid lines in FIG. 1 and in dashed in FIG. 2, or extending through the end wall 12 on the side opposite injection (FIG. 4), or the orifice of a channel bored in a circular element on shaft 13 attached to the piston 6 and extending through the end wall 12 as may be seen in FIG. 2.

According to a general feature of the invention, at least one communication channel is provided between the second chamber 10 and the exterior of the cylinder 5. This channel has a chamber orifice 14 opening into the second chamber and an exterior orifice 15 opening to the exterior. Furthermore, at least one of these two orifices 14 and 15 is positioned in a fashion so as to be blocked or disengaged by the user during the displacement of an element 16 moveably mounted with respect to the cylinder 5 in correspondance with the movements of the second piston 6.

When it is said that the element 16 is moveable in correspondance with piston 6, this is taken to mean that the element 16 has a path equal to that of the piston 6 and, therefore, that every movement of piston 6 in the course of its displacement, and in particular in the direction of injection, accompanies a corresponding movement of the mobile element 16. Preferably, in the course of the injection of the piston 6, the corresponding displacement of the mobile element 16 occurs in the longitudinal direction with respect to the cylinder 5.

The communication channel can include, according to the invention, any passage, having one or multiple paths, in a single section or a plurality of sections which can be positioned between the second chamber 10 and the exterior of the cylinder 5.

In the syringe shown in FIG. 3, numerous communication channels C, C', C'', C''', etc. are illustrated which are bored through the lateral wall of the cylinder 5 along a single surface generator. They are spaced equally or otherwise whose value depends upon the extent of successive movements to which one desires to subject the second piston 6. The mobile element 16 is slideably mounted along the cylinder 5 in a fashion so as to cover the channel C, C', C'', C''', etc.

More exactly, each channel C, C', C'', C''', etc. has a chamber orifice 14 and an exterior orifice 15, and the mobile element is adapted to disengage and then successively block each of the exterior orifices 15 of the channels.

In the example shown in FIG. 2, a single communication channel C is disclosed which meets with a portion of the length of the channel 11A. The inlet orifice 14 of the channel C is in communication with the chamber orifice 11 of the second chamber 10. The shaft 13 has in its end portion a ring 18, hollowed, which constitutes two circular paths of the channel after an inlet nozzle 19 for feeding the gas under pressure. The exterior orifice 15 of the channel C is placed on the interior of the ring 18 in manner so as to be able to be easily blocked or disengaged by the thumb of the user, introduced into this ring 18 in the same fashion as into a conventional ring of a manual syringe. The portion of the shaft 13 positioned between the piston 6 and the ring 18 thus constitues the mobile element 16.

In the examples of FIGS. 1 and 4, the communication channel C comprises a first section C1 extending between the second chamber and the first chamber 9 in passing through the piston 6 and the shaft 7. The second section C2 extends through the wall of the cylinder 5 between the first chamber 9 and the exterior.

The section C1 is bored coaxially in the piston 6 and then extends into the piston shaft 7 and ends in a radial portion in this latter shaft. In the syringe of FIG. 1, the section C1 enters the first chamber 9 through a chamber orifice 20 positioned between the lateral surface of the shaft 7 and the cylinder. The mobile element 16 coaxially traverses the end wall 12 opposite to the injection side of the cylinder 5 and ends on the interior of the cylinder in a conical end member 21 adapted to block the flared orifice 14 of the section C1. Preferably, the conical end 21 has diameter greater than that of the shaft 16 and is held between bent fingers 22 which extend from the surface adjacent to the piston 6. These fingers allow for play in the longitudinal direction at the conical end 21.

In the syringe of FIG. 4, the shaft of piston 7 is provided with a radial extension 23 in which the radial portion of the section C1 extends. This extension 23 is spaced from the piston 6 and the section C1 ends in a chamber orifice 20 positioned on the surface of the extension 23 facing the piston 6. The mobile element 16 extends through the end wall 8, on the injection side of the cylinder 5, and ends at the interior of the cylinder in a small collar 24 slideably mounted on the piston shaft 7 between the piston 6 and the radial extension 23. The small collar 24 has a blocking element 25 adapted to block the opening orifice 20 of the section C1 on the interior of the first chamber 9. The mobile element 16 extends through the end wall 8 of the cylinder 5 and is adaptedd to slide longitudinally along the cartridge 1.

The operation of the device is essentially identical in every case. When the syringe is prepared for use, gas under pressure is channeled through feed channel 11A into the second chamber 10. This gas can have no effect on the piston 6 as long as the channel C or one of the channels C, C', C'', C''', etc. has its two orifices 14 and 15 open or as long as the sections C1 and C2 have their orifices open. As soon as one blocks one of the orifices: the orifice 15 with a finger in the syringe of FIG. 2, the orifice 15 with the mobile elements 16 in the syringe of FIG. 3, the orifice 14 of the section C1 with the assistance of the mobile element 16 respectively in the syringes of FIGS. 1 and 4, the pressure increases in the second chamber 10 and the piston 6 is pushed in the direction of injection. This movement of the piston, and, as a result, the injection of the liquid, stops as soon as the orifice of the communication channel is no longer blocked which occurs very rapidly if the mobile element 16 is not pushed by the user in a manner to accompany the piston 6.

With the syringe of FIG. 2, as soon as the ring 18 moved by the piston 6 has advanced faster than the thumb which blocks the orifice 15, the injection stops. With the syringe of FIG. 3, the mobile element 16 extends to block the orifice 15 of the channel C', as soon as the piston 6 extends past the channel C'' uncovered by the window 17, the injection stops. The same situation occurs with the syringes of FIGS. 1 and 4.

Consequently, the user himself controls the speed of injection by means of the speed at which he displaces the mobile element 16. Furthermore, the user observes and feels in which fashion, slow or fast, the piston 6 performs the injection of the liquid by following the displacement of the mobile element 16. When the diffusion of the liquid 2 occurs with difficulty in a particular tissue, the user displaces the mobile element 16 slowly at a velocity such that the piston 6 can evenly accompany it. In soft tissue, the displacement of the mobile element can be even slower; so as to avoid a sudden brutal injection. This is important when one realizes that the injection of an anesthetic liquid performed too rapidly can cause cardiac problems and if done too suddenly can cause tearing of the tissue.

The extent of movement of the mobile element 16 is the same as that of pistons 6 and 4 and is proportional to the quantity of liquid ejected. As a result, the extent which the user causes the mobile element 16 to travel informs him of the corresponding fraction of liquid ejected. He can therefor accelerate or decelerate, as a result, the movement of the mobile element 16 or even interrupt it so as to make only a partial injection under certain circumstances. The movement can be as slow as necessary so as to provide a precise dosage. Furthermore, the mobile element 16 can comprise a graduated scale if greater accuracy is desired.

Of course, with all hydraulically assisted syringes, the force or fatigue of the user is no longer a factor limiting the injections even when injecting into resistant tissue.

With a syringe according to the invention, the piston is displaced at a speed as slowly as desired by the user over the entire extent of its travel. This does not exclude on the contrary, the possibility of very sudden and rapid injections, because it is easy for the user to push the mobile element 16 at a greater speed than that which would otherwise be assumed by the piston. As a result, injections without needles are possible with the syringe of the invention as well.

The syringes of FIGS. 1–3 are relatively long by virtue of the additional length of the mobile element 16 at the beginning of the injection taken together with that of the cylinders 1 and 5. The syringe of FIG. 4 is shorter and is preferrable in dental applications. In this situation, the mobile element 16 is displaced towards the needle during the injection by means of a finger such as the index finger.

It will be noted that the first chamber 9 has a volume which decreases in the course of injection. It is necessary that this chamber always freely communicate with the atmosphere. According to the invention, it is not necessary that this chamber 9 be filled with pressurized gas so as to equilibrate the pressure exerted on the piston 6 in the second chamber 10. Consequently, when the resistance of the tissue is low, the piston 6 is pushed by the gas under pressure when the orifice of the communication channel is but partially blocked. Total blockage is unnecessary except when the tissue has a high resistance. As a result, with a syringe according to the invention, the force used is ony that which is necessary and the consumption of pressurized gas is economically metered as a function of the application.

In a syringe as has been described in the embodiment of FIG. 4, the piston 6 has a diameter of 26 mm and an orifice 20 having a diameter of 0.3 mm for a gas feed pressure of 4 bars.

The syringe according to the invention is useable for the injection of anesthetic liquids as has been noted above but it is clear that the inventive device is not limited to this use precisely by virtue of its possibility of creating, under the precise and metered control of the operator, a substantial injection force because the energy is furnished by an exterior force.

In particular, dentists presently utilize a viscous paste for taking tooth impressions. Such pastes are prepared when needed by mixing a first silicon based component and a second componenet comprising a softener. After preparation, this paste is introduced into a syringe and ejected with the assistance of the syringe against the teeth and gums whose contour one wishes to copy. The syringe of the invention is perfectly adapted for such an application.

In the embodiments described above, reference is made to a syringe which serves only to produce the injection of a liquid or a paste by means of the controlled displacement of the piston in a desired direction. The invention further extends to include a device adapted to control the movement of the piston so as to cause a controlled aspiration, if desired, for example, so as to produce a strong or sudden suction on the end of a conduit mounted on the body of the syringe. In this instance, it is necessary only to provide a simple inversion of the positioning of the described elements, particularly the direction of the inlet and the outlet of the pressurized fluid and of the displacement of the mobile element controlling the flow of this fluid.

Although the invention has been described with particular reference to specific means and embodiments, it is to be understood that the invention is not limited to the particulars disclosed but extends to all equivalents falling within the scope of the claims.

What is claimed is:

1. Apparatus for injecting or aspirating a fluid, including a liquid or paste, said apparatus comprising:
   (a) a first piston adapted to be in direct contact with said fluid;
   (b) a second piston comprising a shaft adapted to coact with said first piston, said second piston being slideably mounted in a cylinder, said cylinder being divided by said second piston into a first chamber situated on the fluid injection side of said cylinder and a second chamber situated on the opposite side of said cylinder, the cylinder being adapted to be in fluid communication with a positive or negative pressure;
   (c) at least one communication channel positioned between said second chamber and the exterior of said cylinder, said at least one communication channel having a chamber orifice opening into the second chamber and an exterior orifice opening to the exterior; and
   (d) blocking means for blocking said channel;
   whereby a positive or negative pressure in said second chamber relative to said first chamber while said communication channel is blocked results in the controllable movement of said first piston.

2. The apparatus as defined by claim 1 wherein said apparatus is adapted for use as a syringe and wherein said shaft is adapted to push said first piston to inject said fluid in response to a positive pressure within said second chamber.

3. The apparatus as defined by claim 2 wherein said blocking means comprises means for blocking or disengaging at least one of said chamber or exterior orifices.

4. The apparatus as defined by claim 3 wherein said blocking means comprises a mobile element, said mobile element being adaped to move relative to said cylinder.

5. The apparatus as defined by claim 4 wherein said mobile element extends beyond said second piston and outside of said cylinder, and wherein said channel extends into said shaft of said second piston and said exterior orifice is positioned on the outside of said cylinder.

6. The apparatus as defined by claim 5 wherein said shaft extends outside of said cylinder in the form of a circular element, said circular element comprising said exterior orifice whereby said channel may be blocked by placing a thumb over said exterior orifice.

7. The apparatus as defined by claim 6 wherein said shaft extending outside of said cylinder further comprises an orifice for feeding pressurized fluid into said channel to pressurize said second chamber.

8. The apparatus as defined by claim 4 wherein said communication channel comprises a first section extending between the second chamber and the first chamber, said communication channel passing through said second piston, and a second section passing through the wall of said cylinder between said first chamber and the exterior of said cylinder.

9. The apparatus as defined by claim 8 wherein said mobile element passes through the end wall of the cylinder opposite to the injection side and ends on the interior of the cylinder in an end adapted to block the orifice of the communication channel opening into the second chamber.

10. The apparatus as defined by claim 9 wherein the first section of the channel is coaxially bored in the piston and in the shaft of said piston and opens onto the lateral surface of said piston shaft on the interior of the first chamber.

11. The apparatus as defined by claim 8 wherein the mobile element passes through the end wall of the cylinder from the injection side and extends outside of the cylinder parallel thereto, said mobile element comprising a blocking element on the interior of said cylinder, said blocking element being adapted to block the opening of said first section on the interior of said first chamber.

12. The apparatus as defined by claim 11 wherein the first section of the communication channel is bored coaxially through the second piston and the shaft of said second piston, said shaft having a radial extension facing said second piston, the first section leading into said radial extension and ending in an opening in a surface facing said piston, said mobile element extending to face said opening with a projecting portion adapted to move against said piston opening to block said opening.

13. The apparatus as defined by claim 12 wherein said mobile element is provided at its end positioned within said cylinder with a small collar slideably mounted on said shaft of said second piston between the second piston and the radial extension.

14. The apparatus as defined by claim 13 wherein said projecting portion is mounted on said radial collar.

15. The apparatus as defined by claim 3 wherein said exterior orifice is constituted by a plurality of orifices on the wall of said cylinder.

16. The apparatus as defined by claim 15 wherein said mobile element is a sleeve comprising a window, and wherein said sleeve is adapted to slide over said exterior orifices whereby registration of said window with one of said exterior orifices results in the unblocking of said exterior orifice.

17. The apparatus as defined by claim 4 wherein said mobile element comprises a plunger adapted to cooperate with said second piston, said plunger being adapted to extend outside of said cylinder.

18. The apparatus as defined by claim 17 wherein said second piston comprises a first section extending therethrough, said first section allowing for the passage of a fluid between said first and second chambers, and wherein said mobile element ends in a conical member adapted to block said first section.

19. The apparatus as defined by claim 18 wherein said conical member is held by a plurality of fingers extending from said second piston whereby said plunger and second piston move in phase with one another.

* * * * *

UNITED STATES PATENT AND TRADEMARK OFFICE
CERTIFICATE OF CORRECTION

PATENT NO. : 4,323,066

DATED : April 6, 1982

INVENTOR(S) : Frederic BOURDON

It is certified that error appears in the above-identified patent and that said Letters Patent is hereby corrected as shown below:

Abstract, line 13, delete "The".
Abstract, line 13, "at" should be --At--.
Column 1, line 9, delete "a" (second occurrence).
Column 1, line 27, "The" should be --the--.
Column 1, line 46, "by" should be --may--.
Column 2, line 7, delete "the".
Column 2, line 7, "at" should be --At--.
Column 2, line 11, delete "the".
Column 2, line 14, "controlable" should be --controllable--.
Column 2, line 62, "comprises" should be --comprise--.
Column 3, line 36, after "is" insert --a--.
Column 4, line 24, "poston" should be --position--.

UNITED STATES PATENT AND TRADEMARK OFFICE
CERTIFICATE OF CORRECTION

PATENT NO. : 4,323,066

DATED : April 6, 1982

INVENTOR(S) : Frederic BOURDON

It is certified that error appears in the above-identified patent and that said Letters Patent is hereby corrected as shown below:

Column 5, line 44, "constitues" should be --constitutes--.

Column 6, line 12, "adaptedd" should be --adapted--.

Column 6, line 62, "therefor" should be --therefore--.

Signed and Sealed this

Twenty-first Day of September 1982

[SEAL]

Attest:

GERALD J. MOSSINGHOFF

Attesting Officer     Commissioner of Patents and Trademarks